(12) United States Patent
Krawitz

(10) Patent No.: US 7,638,142 B2
(45) Date of Patent: Dec. 29, 2009

(54) THERAPEUTIC COMPOSITION FOR THE TREATMENT OF DRY EYE SYNDROME

(75) Inventor: Paul L. Krawitz, Cold Spring Harbor, NY (US)

(73) Assignee: Vitamin Science, Inc., Huntington, NY (US)

( * ) Notice: Subject to any disclaimer, the term of this patent is extended or adjusted under 35 U.S.C. 154(b) by 0 days.

(21) Appl. No.: 11/546,088

(22) Filed: Oct. 11, 2006

(65) Prior Publication Data

US 2007/0082065 A1    Apr. 12, 2007

Related U.S. Application Data

(60) Provisional application No. 60/725,994, filed on Oct. 12, 2005.

(51) Int. Cl.
*A61K 33/34* (2006.01)
*A61K 35/34* (2006.01)

(52) U.S. Cl. .................... 424/548; 424/635

(58) Field of Classification Search ............. 424/400
See application file for complete search history.

(56) References Cited

U.S. PATENT DOCUMENTS

| | | | |
|---|---|---|---|
| 4,522,803 A * | 6/1985 | Lenk et al. ............. | 424/1.21 |
| 4,804,539 A | 2/1989 | Guo et al. | |
| 5,576,016 A * | 11/1996 | Amselem et al. ............ | 424/450 |
| 5,853,753 A | 12/1998 | Maierhofer et al. | |
| 6,093,706 A | 7/2000 | Zeligs | |
| 6,429,227 B1 | 8/2002 | Schneider et al. | |
| 6,506,412 B2 | 1/2003 | Troyer et al. | |
| 6,566,398 B1 | 5/2003 | Ueno | |
| 7,029,712 B1 | 4/2006 | Thornton et al. | |
| 2002/0095000 A1 | 7/2002 | Troyer et al. | |
| 2002/0099100 A1 | 7/2002 | Troyer et al. | |
| 2004/0058015 A1* | 3/2004 | Tao ........................... | 424/725 |
| 2004/0076695 A1 | 4/2004 | Gilbard | |
| 2005/0249821 A1 | 11/2005 | Paul, Jr. | |

FOREIGN PATENT DOCUMENTS

| EP | 0930072 A1 * | 7/1999 |
|---|---|---|
| WO | WO 2004006801 A2 * | 1/2004 |
| WO | WO 2005084635 A2 * | 9/2005 |

OTHER PUBLICATIONS http://www.nutritiondata.com/facts-C00001-01c20c0.html, NutritionData-Broccoli, raw, Feb. 27, 2008, 7 pages.*
http://www.nutritiondata.com/facts-C00001-01c201B.html, NutritionData-Soybeans, gree, cooked, boiled, drained, with salt, Feb. 27, 2008, 7 pages.*
Vesper et al., Sphinglipids in Food and the Emerging Importance of Sphingolipids to Nutrition, 1999, Journal of Nutrition, 129 (7), 1239-1250.*
Http://www.chem.qmul.ac.uk/iupac/misc/glycp.html, nomenclature of glycoproteins, glycopeptides and peptidoglycans, 1985 Recommendations-printed Feb. 27, 2008, 10 pages.*
Jaga, Risk reduction for DDT toxicity and carcinogenesis through dietary modification, 2001, The Journal of the Royal Society for the Promotion of Health, vol. 121, No. 2, Abstract, 1 page.*
http://www.cancerlynx.com/chinesedata.html, CancerLynx, printed Feb. 28, 2008, 14 pages.*
http://www.florahealth.com/flora/home/Canada/HealthInformation/Encyclopedias/GinsengRoot(Asian).htm, Herb & Supplement Encyclopedia:Ginseng Root (Asian), printed Feb. 28, 2008, 3 pages.*
http://www.e2121.com/herb_db/viewherb.php3?viewid=101, Rehmannia Root, ENaturalHealthCenter.com, printed Feb. 28, 2008, 4 pages.*
Tahvonen et al., Black currant seed oil and fish oil supplements differ in their effects on fatty acid profiles of plasma lipids, and concentrations of serum total and lipoprotein lipids, plasma glucose and insulin, Jun. 2005, The Journal of Nutritional Biochemistry, vol. 16, Issue 6,353-359.*
Helen's Kitchen-Simple Health, Helen's Kitchen Chicken Flavor Tofu Steaks, Jul. 14, 2004, http://www.helensfoods.com/news/anmviewer.asp?a=1&z=7, printed Sep. 22, 2008, 2 pages.*
www.lionsgrip.com, Curry Powder:What Curry Powder Is, Jun. 25, 2003, www.lionsgrip.com printed from http://web.archive.org/web/20030625131716/http://www.lionsgrip.com/curcurry.html on Sep. 22, 2008, 5 pages.*

\* cited by examiner

*Primary Examiner*—Frederick Krass
*Assistant Examiner*—Gigi Huang
(74) *Attorney, Agent, or Firm*—Dilworth & Barrese, LLP

(57) ABSTRACT

A composition and method for treating dry-eye syndrome and symptoms of vitreous opacities in a host comprising the oral administration of a composition which contains a pharmacologically effective amount of essential fatty acids, polar phospholipids, vitamins, minerals and dietary supplements.

2 Claims, No Drawings

THERAPEUTIC COMPOSITION FOR THE TREATMENT OF DRY EYE SYNDROME

CROSS REFERENCE TO RELATED APPLICATION

This application claims the benefit under 35 U.S.C. §119(e) to Provisional Application No. 60/725,994, filed Oct. 12, 2005 and entitled "TREATMENT OF DRY EYE SYNDROME," the contents of which are incorporated by reference herein.

FIELD OF THE INVENTION

The present invention relates to a therapeutic composition and the treatment and prevention of dry eye syndrome. More specifically, this invention relates to a composition and methods of treating and preventing dry eye syndrome and the visual symptoms of vitreous opacities by therapeutically enhancing the amount of hydration on mucosal surfaces of the eyes.

BACKGROUND OF THE INVENTION

Dry-eye syndrome is a common condition affecting approximately one in five Americans. Dry eye is characterized by a decrease in tear production or an increase in tear film evaporation, together with the ocular surface disease that results. Symptoms include dry, irritated eyes, excessively watery eyes, burning and stinging, a foreign body sensation, and blurred vision. Despite the diverse causes of dry eye syndrome, in all dry eye conditions the ocular surface epithelium undergoes squamous metaplasia, manifested by loss of goblet cells, mucin deficiency and keratinization. These changes result in tear film instability, which leads to the clinical symptoms of dry eye syndrome.

Dry eye syndrome typically results from deficiency in the quality or quantity of tears produced by the patient. Precorneal tear film has traditionally been considered to have a three-layered structure. The closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sciera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contra-indications and incompatibility with soft contact lenses.

Further, the use of medications, such as, 5-methyl-isoxazole-4-carboxylic acid anilides, hydroxyethylidene-cyano acetic acid anilide derivatives, and 2-(4-chlorobenzoylamino)-3-(2-quinolon-4-yl)propionic acid for the treatment xerophthalmia syndrome ("dry eyes") has been attempted with limited results.

Another common disorder of the eyes is "vitreous opacities," commonly known as "eye floaters" or "specks in the eye." They are annoying visual disturbances, often accompanied by flashes of light which are caused by deposits of various size, shape, consistency, refractive index, and motility within the eye's normally transparent vitreous humour. They may be of embryonic origin or acquired due to degenerative changes of the vitreous humour or retina. The perception of floaters is known as myodesopsia, or less commonly as myiodeopsia, myiodesopsia, or myodeopsia. When observed subjectively, floaters are entoptic phenomena characterized by shadow-like shapes which appear singly or together with several others in one's field of vision. They may appear as spots, threads, or fragments of cobwebs, that float slowly before one's eyes.

Floaters are not uncommon, however, floaters are more than a nuisance and a distraction to those with severe cases, especially if the spots seem to constantly drift through the field of vision. The shapes are shadows projected onto the retina by tiny structures of protein or other cell debris discarded over the years and trapped in the vitreous humour.

Treatments include, among others, vitrectomy for more severe cases, however, the procedure is typically not warranted in those with lesser symptoms due to the potential for complications as severe as blindness. Another treatment is laser vitreolysis. This procedure can be time consuming and there is no consensus as to how completely effective it is.

Due to the complex pathologies of "dry eye" syndrome and "vitreous opacities," current therapies, e.g., eye drop preparations and the like, provide only temporary medical measures, thus the need for effective medical treatment of the symptoms of "dry eye" and "vitreous opacities" still remains.

SUMMARY OF THE INVENTION

An object of the present invention is to provide an orally administered composition for the treatment of dry-eye syndrome, said composition comprising an effective dry-eye syndrome treatment amount of a mixture of water-soluble antioxidant, water-insoluble antioxidant, essential fatty acid, glycoprotein complex, phospholipid, phytosterol, curcuminoid, and at least one micronutrient cofactor selected from the group consisting of vitamin B6 and copper.

Another object of the invention is to provide a method of treating dry-eye syndrome in a host, said method comprising administering orally to said host a composition comprising an effective dry-eye syndrome treatment amount of a mixture of water-soluble antioxidant, water-insoluble antioxidant, essential fatty acid, glycoprotein complex, phospholipid, phytosterol, curcuminoid, and at least one micronutrient cofactor selected from the group consisting of vitamin B6 and copper.

Yet another object of the invention is to provide a method of treating the symptoms of vitreous opacities in a host, said method comprising administering orally to said host a composition comprising an effective vitreous opacities symptoms treatment amount of a mixture of water-soluble antioxidant, water-insoluble antioxidant, essential fatty acid, glycoprotein complex, phospholipid, phytosterol, curcuminoid, and at least one micronutrient cofactor selected from the group consisting of vitamin B6 and copper.

The composition of the present invention when administered orally in an effective amount provides relief from the symptoms associated with dry eye syndrome and vitreous opacities.

DESCRIPTION OF THE INVENTION

The present invention provides relief of dry eye symptoms with an inventive combination of natural ingredients that perform synergistically. The combination improves dry eye syndrome by: replenishing the inner mucus layer of the tear film with mucin and the outer fatty lipid layer with phytosterols; reduction of lacrimal gland inflammation, resulting in improved tear production and reduced tear film surface tension with a blend of DHA and EPA Omega 3 essential fatty acids, ALA Omega 3, GLA Omega 6, lactoferrin, vitamin E mixed tocopherol oils, and Circumin (a the natural COX2 inhibitor); and improved tear film stability with polar phospholipids, phosphatidyl ethanolamine, phosphatidyl serine, and sphingomyelin.

Furthermore, the present invention provides a method for the treatment of the symptoms related to "vitreous opacities," commonly known as "specks in the eye" or "eye floaters," through stabilization of the tear film with the composition of the present invention.

The method of manufacturing the composition of the present invention includes procedures that one skilled in the art of Good Manufacturing Procedure (GMP) and production of high quality pharmaceutical formulations would use. The method comprises blending together each of the following ingredients: vitamin C, vitamin E, Vitamin B-6, copper, alpha linolenic acid, docosahexaenoic acid, eicosapentanoic acid, gamma linolenic acid, lactoferrin, mucin complex, phosphatidylethanolamine, phosphatidylserine, phytosterols, sphingomyelin, and turmeric extract into a suitable dosage form and in appropriate quantities. The method includes the use of know and conventional manufacturing excipients, e.g., flavorants, preservatives, stabilizers, and the like.

According to one embodiment of the present invention, the preparation is preferably administered as two capsules twice daily with meals. However, it should be understood that the word "composition," "preparation" or "formulation" as used herein is intended to refer collectively to these ingredients (i.e., components or compounds) and amounts whether taken separately by a patient or whether included in a single capsule or other ingestible medium. Suitable dosage forms include all dosage forms know in the art, such as, for example, capsules, tablets, liquids, sublingual forms and the like.

The terms "ingredient," "component" and "compound," as understood herein, refer to the pharmacologically active antioxidants and micronutrients and substances that comprise the composition of the invention.

The phrase "effective amount" is used throughout the specification to describe concentrations or amounts of the component ingredients according to the present invention which may be used to produce a favorable change in the symptomology, disease or condition treated, whether that change is a decrease in or reversal of the effects of symptomology or disease state depending upon the disease state or condition treated. In the present invention, in preferred aspects, an effective amount is that amount which is used to treat the symptomology associated with dry eye syndrome and vitreous opacities. The total daily effective treatment/prevention amount can be administered in one capsule or dosage form, or preferably in divided doses or multiple capsules, which in total, deliver the effective amount of the composition of the present invention.

In one embodiment of the present invention, a preparation for treating dry eye syndrome, the preparation of the invention includes the following components:
  Vitamin C (from calcium ascorbate)
  Vitamin E (as mixed tocopherols)
  Vitamin B-6 (as pyridoxal 5' phosphate)
  Copper (as cupric oxide)
  Alpha Linolenic acid (from flaxseed oil)
  docosahexaenoic acid (DHA from purified fish oil)
  Eicosapentanoic acid (EPA from purified fish oil)
  Gamma linolenic acid (from borage oil)
  Lactoferrin
  Mucin complex (porcine) (minimum 60% mucin, a source of mucopolysaccharides)
  Phosphatidylethanolamine (from soy leccithin)
  Phosphatidylserine
  Phytosterols (from vegetable oils)
  (Typical distribution: B-Sitosterol 40-58%, Campesterol 20-30%, Stigmasterol 14-22%, Brassicasterol 0-6%, Sitostanol 0-5%)
  Sphingomyelin (from eggs)
  Turmeric extract (curcuma longa) (rhizome)[standardized for 95% curcuminoids(71 mg)]

According to one specific embodiment of the present invention, the preparation is administered as four (4) gelcaps daily in divided doses with meals (it should be understood that the word "composition," "preparation" or "formulation" as used herein is intended to refer collectively to these substances and amounts whether taken separately by a patient or whether included in a single capsule or other ingestible medium).

The above is a preferred form of the treatment of the invention, but variations are possible. The above formulation addresses not only the adequate production of aqueous tears, the middle layer of a healthy tear film on the eye, but also the slippery substances which comprise the inner layer directly coating the epithelium and the outer oily layer over the aqueous tear layer, which helps prevent evaporation. The ranges indicated herein for the various components are probable approximate limits as projected from research and the applicants' knowledge of the functional role played by each substance.

Essential fatty acids are fatty acids that are required in the human diet. This means they cannot be synthesized by the body from other fatty acids and must be obtained from food or supplemental sources. Omega-3 and omega-6 fatty acids, as well as gamma-linolenic acid (GLA) regulate membrane fluidity and membrane function, serve as precursors to eicosanoids (prostaglandins, thromboxanes, and leukotrienes), exhibit enzyme-like activities, and serve as substrates for enzymes, helping to prevent the drying and atrophy of tear glands.

Omega-3 fatty acid is an "essential" fatty acid, and in one embodiment of the invention is administered in amounts of about 500 mg daily. Commercially it is derived from fish oil, microalgae, and certain plant foods such as flax seed, borage, evening primrose and currant oils.

Omega-3s reduce formation of the hormonelike prostaglandins which trigger inflammatory processes. They do this by replacing excessive omega-6 fatty acids, which readily oxidize into free radicals. Pyridoxal 5-phosphate is the active form of vitamin B6. It is necessary for the normal activity of the enzyme delta-6-desaturase, which converts cis-linoleic acid to GLA, and GLA into the precursor of PGE1, dihomo-gamma-linolenic acid. Vitamin B6, or pyridoxal 5-phosphate, is thus a micronutrient cofactor supporting and enhancing conversion of linoleic acid to gamma linolenic acid (GLA).

In one embodiment of the invention, vitamin B-6 is present in the composition in an amount of from about 0.5 mg to about 10 mg, and in another embodiment, vitamin B-6 is present in the composition in an amount of about 4 mg.

Vitamin C is required for the conversion of dihomo-gamma-linolenic acid into prostaglandin E1, and thus is critical for tear production. Ascorbic acid in tears serves an antiflammatory role in the eye's defense system. Vitamin C could be replaced by another water-soluble antioxidant, but vitamin C is preferred.

There is no known optimal daily dose of Vitamin C, although the U.S. recommended daily allowance (RDA) is 60 mg. However, dosages of 2.0 grams and more have frequently been taken as a supplement for general health. In one embodiment of the present invention, vitamin C is present in the composition in the form of ascorbic acid and in an amount of about 10 mg to about 200 mg. In another embodiment of the invention, vitamin C is present in the composition in the amount of about 60 mg.

The essential fatty acids of the invention include, but are not limited linolenic acid, which is the shortest chain omega-3 fatty acid, docosahexaenoic acid (DHA), eicosapentanoic acid (EPA), and linoleic acid, the shortest chain omega-6 fatty acid. The most common fatty acids of each class are linolenic (18:3), EPA (20:5), DHA (22:6) for omega-3 and linoleic (18:2) and arachidonic (20:4) for omega-6.

According to one embodiment of the present invention, alpha linolenic acid is present in the composition in an amount of about 100 mg to about 1000 mg, preferably in an amount of about 500 mg. In another one embodiment of the invention, docosahexaenoic acid is present in an amount of about 100 mg to about 500 mg, preferably in an amount of about 160 mg. In yet another embodiment of the invention, eicosapentanoic acid is present in an amount of about 100 mg to about 500 mg, preferably in an amount of about 240 mg. Still in another embodiment of the invention, gamma linolenic is present in the composition in an amount of about 100 mg to about 600 mg, preferably in an amount of about 300 mg.

Tocopherol, or Vitamin E is a fat-soluble vitamin in eight forms that is a powerful biological antioxidant. Vitamin E acts to protect cells against the effects of free radicals, which are potentially damaging by-products of the body's metabolism. Free radicals can cause cell damage that may contribute to the development of mucosal tissue disease. Vitamin C and other anti-oxidants recycle vitamin E end-products back into effective suppressors of free radicals. Vitamin E exists in eight different forms or isomers, four tocopherols and tocotrienols. All isomers have a chromanol ring, with a hydroxyl group which can donate a hydrogen atom to reduce free radicals and a hydrophobic side chain which allows for penetration into biological membranes. In one embodiment of the present invention, mixed tocopherols are used in the inventive formulation for the treatment of dry-eye syndrome.

In another embodiment of the present invention, vitamin E is present in the composition in an amount of about 5 IU to about 100 IU. In yet another embodiment of the invention, vitamin E is present in the composition in the amount of about 30 IU.

Copper is an essential trace element and micronutrient for humans and animals. In the body, copper shifts between the cuprous and the cupric forms, though the majority of the body's copper is in the cupric form. The ability of copper to easily accept and donate electrons explains its important role in oxidation-reduction (redox) reactions and the scavenging of free radicals. Copper is a critical functional component of a number of essential enzymes, known as cuproenzymes. Copper is known to play an important role in the development and maintenance of immune system function, but the exact mechanism of its action is not yet known. In one embodiment of the present invention, copper is provided in the form of copper oxide in an amount of about 0.1 mg to about 5 mg, and preferably in an amount of about 1 mg.

The pre-ocular tear film is a complex biochemical fluid produced by the lacrimal glands and epithelial cells on the ocular surface. The symptoms of dry eye syndrome may result from deficiencies and disturbances of the mucin network. For example, aqueous tear deficiencies lead to the ocular surface disorder, keratoconjunctivitis sicca (Sicca), is a dry eye syndrome. Sicca results from abnormal terminal differentiation of the ocular surface epithelium and is associated with a marked reduction in mucin production by the goblet cells. The inclusion of mucin in the preferred form of the preparation is to directly supply mucin glycoproteins for the maintenance of the mucin network layer in the tear film. The mucin preferably is from an animal source.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes. These mucins provide lubrication, and additionally attract and hold moisture and sebaceous material for lubrication and the corneal refraction of light.

In one embodiment of the present invention, mucin complex is present in the composition in an amount of about 100 mg to about 200 mg. In another embodiment of the present invention, mucin complex is present in an amount of about 100 mg.

Lactoferrin is a globular protein found in many mucosal secretions such as tears. Its molecular atomic mass is 80,000 u (80 kD). This protein belongs to the transferrin family proteins (transferrin, melanotransferrin, ovotransferin, etc.) showing a high affinity by iron (ferric state). Lactoferrin is a multifunctional protein with antimicrobial activity (bacteriocide, fungicide) and is part of the innate defense proteins mainly at mucoses. This protein is present in secondary granules of polymorphonuclear neutrophils (PMN) and also is secreted by some acinar cells. It has been reported lactoferrin-derived peptides (e.g. lactoferricin, kaliocin-1) with antimicrobial activity.

In one embodiment of the present invention, lactoferrin is present in the composition in an amount of about 5 mg to about 20 mg. In another embodiment of the present invention lactoferrin is present in an amount of about 10 mg.

Amphiphilic lipids, in general, and phosphatidylethanolamine, in particular, are major constituents of cell membranes. These molecules form a phospholipid bilayer with their hydrophilic (polar) heads facing their aqueous surroundings (e.g., the cytosol) and their hydrophobic tails facing each other.

Suitable phospholipids include but are not limited to phosphatidylethanolamine, phosphatidylcholine, phosphatidylserine, phospatidylinositol and sphingomyelin, and the like and mixtures thereof. In one embodiment of the present invention, the phospholipids are phosphatidylethanolamines, phosphatidylserine and sphingomyelin. Phospholipids are available from a variety of natural sources and may be synthesized by methods known in the art.

In one embodiment of the invention, phosphatidylethanolamine is present in the composition in an amount of about 1 mg to about 10 mg, and preferably in an amount of about 5 mg. In another embodiment of the invention, phosphatidylserine is present in the composition in an amount of about 1 mg to about 20 mg, and preferably in an amount of about 20 mg. In yet another embodiment of the invention, sphingomyelin is present in the composition in an amount of about 0.5 mg to about 3 mg, preferably in an amount of about 1 mg.

Phytosterols are a group of compounds structurally very similar to cholesterol, and form a major component of Melbomain Gland secretions. The phytosterols occurring most frequently in the nature are sitosterol, campesterol and stigmasterol. In all phytosterol preparations sitosterol the main component, and typically have a distribution of: B-Sitosterol 40-58%, Campesterol 20-30%, Stigmasterol 14-22%, Brassicasterol 0-6%, Sitostanol 0-5%. The phytosterols may also use lipids as a carrier, and this may be the means by which they are absorbed by the mucosal cells of the small intestine. In one embodiment of the present invention, phytosterol is present in the composition in an amount of about 100 mg to about 1000 mg, and preferably in an amount of about 500 mg.

The curcuminoids have been found to have antioxidant and anti-inflammatory activities. Obtained from turmeric, which includes curcuminoids, such as curcumin (diferuloylmethane), desmethoxycurcumin (hydroxycinnamoyl feruloylmethane), and bis-desmethoxycurcumin (dihydroxydicinnamoyl methane) and mixtures thereof. In one embodiment of the invention, tumeric extract is present in the formulation in an amount of about 25 mg to about 150 mg. In another embodiment of the invention, tumeric extract is present in an amount of about 75 mg.

The ingredients of the inventive formulation work synergistically to help replenish the inner tear layer with mucin and the outer layer with phytosterols; add polar phospholipids, phosphatidylethanolamine, phosphatidylserine, sphingomyelin to the tear composition and thereby improve tear film stability; and reduce lacrimal gland inflammation, resulting in improved tear production and reduced tear film surface tension.

Typically the composition of the present invention may include pharmaceutically acceptable components such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like. Diluents and other additives such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed.

The formulation of the invention can be prepared by standard techniques known in the art. As appreciated by the skilled artisan, the desired processing technique will vary depending upon the exact types and amounts of ingredients present, processing temperature, and the like.

The formulation of the invention may also contain flavorants such as fruit and/or other similar flavors, caramel, and the like. When present, flavorants are typically present in an amount of about 0.005 to about 0.3 mg/ml, more typically about 0.05 to about 0.1 mg/ml.

The formulation of the invention optionally can also contain other ingredients such as preservatives (e.g., sodium benzoate, methyl paraben, ethyl paraben, propyl paraben, and the like), stabilizers (e.g., ferric ammonium citrate, ferrous sulfate, and the like), etc.

Having described the invention in detail, it will be apparent that numerous modifications and variations are possible.

The following examples are offered only to illustrate the invention, and should not be interpreted as a limitation thereon.

EXAMPLE 1

Preparation of Compositions of the Invention:
Formulation I
Vitamin C (from calcium ascorbate) 60 mg
Vitamin B6 (from pyridoxal 5' phosphate) 4.0 mg
Vitamin E (as mixed tocopherols) 30 IU
Copper (as cupric oxide) 1 mg
Alpha Linolenic acid (from flaxseed oil) 500 mg
docosahexaenoic acid (DHA from purified fish oil) 160 mg
Eicosapentanoic acid (EPA from purified fish oil) 240 mg
Gamma linolenic acid (from borage oil) 300 mg
Lactoferrin 10 mg
Mucin complex (porcine) (minimum 60% mucin, a source of mucopolysaccharides) 100 mg
Phosphatidylethanolamine (from soy leccithin) 5 mg
Phosphatidylserine 10 mg
Phytosterols (from vegetable oils)
(Typical distribution: B-Sitosterol 40-58%, Campesterol 20-30%, Stigmasterol 14-22%, Brassicasterol 0-6%, Sitostanol 0-5%) 500 mg
Sphingomyelin (from eggs) 1 mg
Turmeric extract (curcuma longa) (rhizome) [standardized for 95% curcuminoids (71 mg)] 75 mg The composition of Example 1 provides a safe and effective composition for the treatment and symptomatic relief of dry-eye syndrome ("xerophthalmia") and vitreous opacities in a patient in need of such treatment.

Obviously, other modifications and variations of the present invention are possible in light of the above teachings. It is, therefore, to be understood that changes may be made in the particular embodiments described above which run within the full intended scope of the invention.

The invention claimed is:

1. An orally administered composition for the treatment of dry-eye syndrome, said composition comprising an effective dry-eye syndrome treatment amount of a mixture containing vitamin C in an amount from about 10 mg to about 200 mg, vitamin E in an amount from about 5 IU to about 100 IU, vitamin B-6 as pyridoxal 5' phosphate in an amount from about 0.5 mg to about 10 mg, copper as cupric oxide in an amount from about 0.1 mg to about 5 mg, alpha linolenic acid in an amount from about 100 mg to about 1000 mg, docosahexaenoic acid in an amount from about 100 mg to about 300 mg, eicosapentanoic acid in an amount from about 100 mg to about 400 mg, gamma linolenic acid in an amount from about 100 mg to about 600 mg, lactoferrin in an amount from about 5 mg to about 20 mg, mucin complex having a minimum of 60% mucin in an amount from about 10 mg to about 200 mg, phosphatidylethanolamine in an amount from about 1 mg to about 10 mg, phosphatidylserine in an amount from about 1 mg to about 20 mg, phytosterols in an amount from about 100 mg to about 1000 mg, sphingomyelin is present in an amount from about 0.5 mg to about 3 mg, and turmeric extract is present in an amount from about 25 mg to about 150 mg.

2. The composition of claim 1 wherein the vitamin C is present in an amount of about 60 mg, the vitamin E is present in an amount of about 30 IU, the vitamin B-6 is present as pyridoxal 5' phosphate in an amount of about 4 mg, the copper is present as cupric oxide in an amount of about 1 mg, the alpha linolenic acid is present in an amount of about 500 mg, the docosahexaenoic acid is present in an amount of about 160 mg, the eicosapentanoic acid is present in an amount of about 240 mg, the gamma linolenic acid is present in an amount of about 300 mg, the lactoferrin is present in an amount of about 10 mg, the mucin complex is present in an amount of about 100 mg, the phosphatidylethanolamine is present in an amount of about 5 mg, the phosphatidylserine is present in an amount of about 10 mg, phytosterols are present in an amount of about 500 mg, the sphingomyelin is present in an amount of about 1 mg, and the turmeric extract is present in an amount of about 75 mg.

* * * * *